(12) United States Patent
Weiner et al.

(10) Patent No.: US 10,905,574 B2
(45) Date of Patent: Feb. 2, 2021

(54) ENDOLUMINAL STENTS AND METHODS OF DELIVERY

(71) Applicant: Boston Scientific Scimed, Inc., Maple Grove, MN (US)

(72) Inventors: Jason Weiner, Grafton, MA (US); Dane T. Seddon, Boston, MA (US); Sean P. Fleury, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 137 days.

(21) Appl. No.: 15/898,710

(22) Filed: Feb. 19, 2018

(65) Prior Publication Data

US 2018/0168835 A1    Jun. 21, 2018

Related U.S. Application Data

(63) Continuation of application No. 14/725,655, filed on May 29, 2015, now Pat. No. 9,918,858.

(60) Provisional application No. 62/005,314, filed on May 30, 2014.

(51) Int. Cl.
| | |
|---|---|
| *A61F 2/92* | (2013.01) |
| *A61F 2/95* | (2013.01) |
| *A61F 2/915* | (2013.01) |
| *A61F 2/04* | (2013.01) |
| *A61F 2/966* | (2013.01) |

(52) U.S. Cl.
CPC .................. *A61F 2/92* (2013.01); *A61F 2/95* (2013.01); *A61F 2/915* (2013.01); *A61F 2/966* (2013.01); *A61F 2002/046* (2013.01); *A61F 2002/9155* (2013.01); *A61F 2002/91541* (2013.01); *A61F 2002/91575* (2013.01); *A61F 2210/0076* (2013.01); *A61F 2230/0013* (2013.01)

(58) Field of Classification Search
USPC ........................................ 623/1.1–1.35, 1.37
See application file for complete search history.

(56) References Cited

U.S. PATENT DOCUMENTS

| | | | |
|---|---|---|---|
| 5,007,926 | A | 4/1991 | Derbyshire |
| 5,258,027 | A | 11/1993 | Berghaus |
| 5,366,504 | A | 11/1994 | Andersen et al. |
| 5,383,926 | A | 1/1995 | Lock et al. |

(Continued)

FOREIGN PATENT DOCUMENTS

| | | |
|---|---|---|
| EP | 2698126 A1 | 2/2014 |
| WO | 2002055125 A2 | 7/2002 |

*Primary Examiner* — Yashita Sharma
(74) *Attorney, Agent, or Firm* — Seager, Tufte & Wickhem, LLP

(57) ABSTRACT

An endoluminal stent and associated methods for placing the endoluminal stent in a lumen of a trachea of a patient. The stent includes an elongate framework having a first open end, a second open end opposite the first open end, and a lumen extending from the first open end to the second open end. The elongate framework includes a first edge extending from the first open end to the second open end, a second edge extending from the first open end to the second open end, and an opening between the first edge and the second edge extending from the first open end to the second open end such that the stent has a C-shaped cross-section. The stent may be implanted in a trachea with the opening positioned along a posterior wall of the trachea adjacent the trachealis muscle.

18 Claims, 12 Drawing Sheets

(56) References Cited

U.S. PATENT DOCUMENTS

| | | | |
|---|---|---|---|
| 5,480,431 A | | 1/1996 | Freitag et al. |
| 5,824,038 A | * | 10/1998 | Wall ........................ A61F 2/92 |
| | | | 623/1.12 |
| 5,928,261 A | | 7/1999 | Ruiz |
| 7,647,931 B2 | | 1/2010 | Pflueger et al. |
| 8,578,938 B2 | | 11/2013 | Pflueger et al. |
| 2003/0149488 A1 | | 8/2003 | Metzger et al. |
| 2008/0065209 A1 | | 3/2008 | Pflueger |
| 2010/0010620 A1 | | 1/2010 | Weber |
| 2010/0262216 A1 | | 10/2010 | Xue |

* cited by examiner

ENDOLUMINAL STENTS AND METHODS OF DELIVERY

CROSS-REFERENCE TO RELATED APPLICATIONS

This application is a continuation of U.S. application Ser. No. 14/725,655, filed May 29, 2015, which claims priority to U.S. Provisional Application No. 62/005,314, filed May 30, 2014, the entire disclosures of which are herein incorporated by reference.

TECHNICAL FIELD

Some embodiments relate to medical devices, and methods for manufacturing and using the same. More particularly, the present disclosure relates to devices such as stents for supporting body structures such as tracheae and/or preventing or resisting collapsing of body structures such as tracheae.

BACKGROUND

In general, the human body includes various lumens, such as a trachea, arteries, blood vessels, as well as urinary, biliary, esophageal or renal tracts, etc. These lumens sometimes become occluded or weakened, or otherwise in need of structural support. For example, the body lumen can be constricted by a tumor, occluded by plaque, or weakened by an aneurysm. For instance, tracheobronchomalacia or TBM is a condition characterized by flaccidity of the cartilage that supports the trachea. This leads to tracheal collapse which in some instances may extend further to the bronchi. TBM may cause discomfort in swallowing, coughing, and breathing to the patient. However, such a condition of the patient can be treated with a medical endoprosthesis to help support the trachea.

Endoprostheses have been developed that may be implanted in a passageway or lumen in the body. In general, such endoprostheses are tubular members with a circular cross-section, examples of which include stents, stent grafts, covered stents, etc. However, such endoprostheses may not be suitable for lumens such as tracheae having non-circular cross-sections, such as a D-shaped cross-section, which requires continued functionality of the trachealis muscle to permit the flow of mucus therethrough, for example.

For instance, the trachea, which lies adjacent to esophagus, has a flat posterior wall which may be pressed by a circular stent, impeding the functionality of the trachealis muscle. In some other instances, existing stents may not be suitable for deployment in branching airways, as the stenting may block side branching airways in the bronchi, for example. In addition, the stents may not allow mucus clearing. Hence, there may exist a need of stents or endoprostheses that may provide desired luminal support while preserving other functionality of the body lumen.

SUMMARY

One illustrative embodiment is an endoluminal stent. The endoluminal stent includes an elongate framework. The elongate framework has a first open end, a second open end and opposite the first open end, and a lumen extending from the first open end to the second open end. The elongate framework includes a first edge extending from the first open end to the second open end, a second edge extending from the first open end to the second open end, and an opening between the first edge and the second edge. The opening can extend continuously from the first open end to the second open end.

Another illustrative embodiment is an endoluminal stent. The endoluminal stent includes an elongate framework. The elongate framework has a first open end, a second open end opposite the first open end, and a lumen extending along a longitudinal axis from the first open end to the second open end. The elongate framework has a C-shaped cross section in a plane perpendicular to the longitudinal axis.

Another illustrative embodiment is a method of placing a stent in a lumen of a trachea. The method can include inserting a stent in a lumen of a trachea. The stent can include an elongate framework having a first open end, a second open end opposite the first open end, a lumen extending along a longitudinal axis from the first open end to the second open end, and an opening between opposing longitudinal edges of the elongate framework. The opening can extend continuously from the first open end to the second open end. The method can include orienting the stent in the lumen of the trachea such that the opening is positioned along a posterior wall of the trachea adjacent a trachealis muscle.

Yet another illustrative embodiment is an endoluminal stent. The endoluminal stent includes an elongate framework. The elongate framework has a first open end, a second open end opposite the first open end, and a lumen extending from the first open end to the second open end. The elongate framework includes a first edge extending from the first open end to the second open end, a second edge extending from the first open end to the second open end, and an opening extending continuously from the first open end to the second open end.

The above summary of some embodiments is not intended to describe each disclosed embodiment or every implementation of the present disclosure. The Figures, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which.

DETAILED DESCRIPTION

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the same reference numbers. The drawings, which are not necessarily to scale, depict illustrative embodiments and are not intended to limit the scope of the disclosure.

Figure 1:
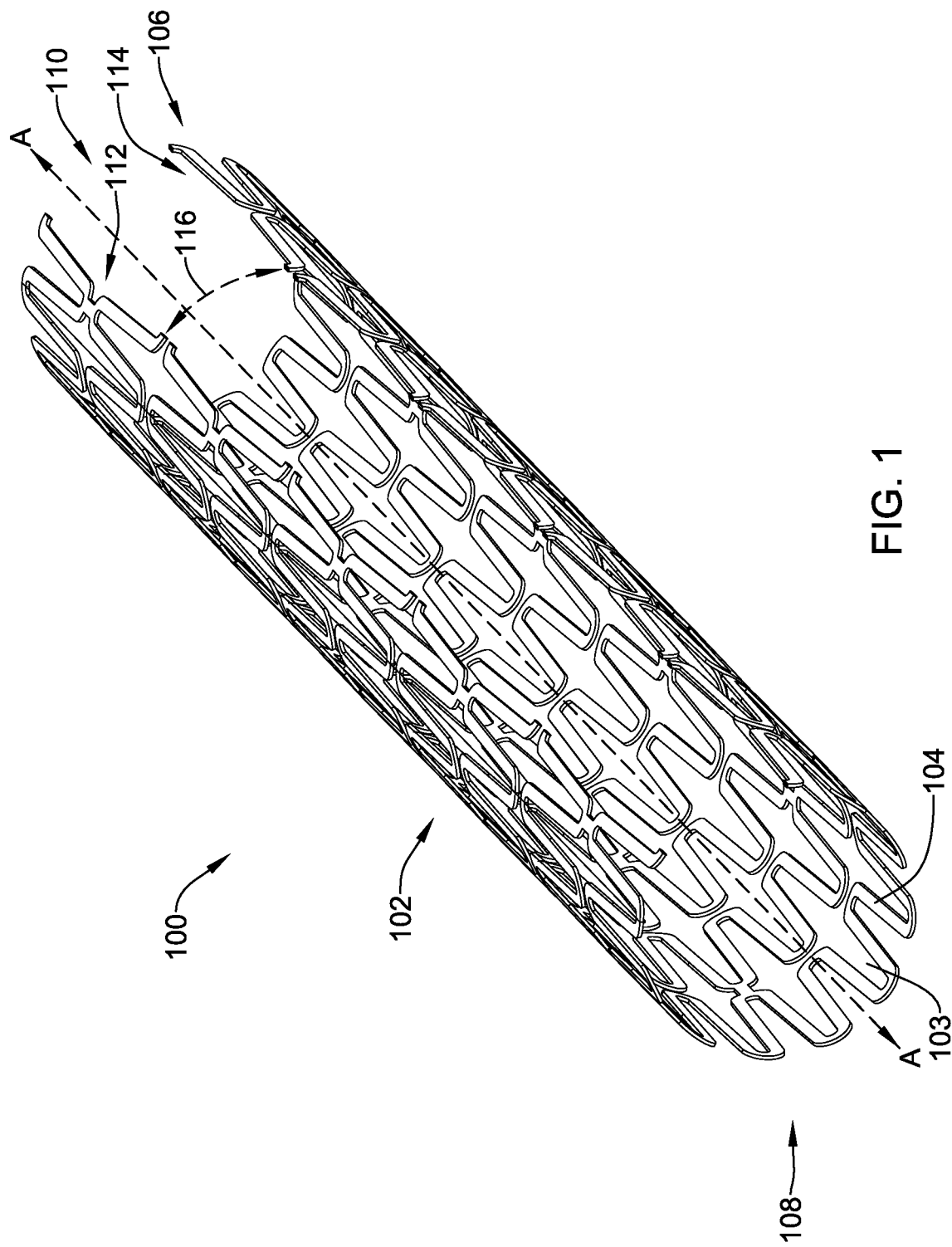
FIG. 1 is a perspective view of an exemplary endoluminal stent, in accordance with some embodiments of the present disclosure.

FIG. 1 is a perspective view of an exemplary endoluminal stent 100. The endoluminal stent 100 may include an elongate framework 102. In some instances, the framework 102 may include a plurality of interstices 103 formed between adjacent segments of the framework 102. For example, in some instances the framework 102 may include a number of interconnected struts 104 defining a plurality of interstices 103 therebetween.

The framework 102 may include a first open end 106, a second open end 108 opposite the first open end 106, and a lumen 110 extending between the first open end 106 and the second open end 108. In some embodiments, the length of the framework 102 may depend upon the length of the lumen in which the framework 102 may be inserted. The framework 102 may include a first edge 112, a second edge 114, each extending from the first open end 106 to the second open end 108, and an opening 116 between the first edge 112 and the second edge 114 that extends continuously from the first open end 106 to the second open end 108. In some instance, the framework 102 may include one or more, or a plurality of bridge members extending across the opening 116 between the first edge 112 and the second edge 114. The first edge 112 may be a substantially straight edge parallel to the longitudinal axis A. However, it is understood that the first edge 112 may be angled or curved, if desired. Similarly, the second edge 114 may be a substantially straight edge extending parallel to the longitudinal axis A. However, it is understood that the second edge 114 may be angled or curved, if desired. The first edge 112 may extend generally parallel to the second edge 114, in some instances, or the first edge 112 may be nonparallel to the second edge 114, if desired.

The opening 116 may be sized to align with the size of a posterior wall of a trachea. For example, the width of the opening may be about the width of the posterior wall of a trachea in some instances.

The framework 102 may be flexible such that size of the opening 116 can be adjusted by the application of force on the framework 102 by the user or when the endoluminal stent 100 comes in contact with the lumen walls (not shown). In some embodiments, the opening 116 can be contracted by moving the first and second edges 112, 114 past each other, for example, in an overlapping or spiral pattern. An example of such a configuration that may have a small delivery footprint will be discussed in detail with reference to FIG. 7A.

In some embodiments, the framework 102 may form an open structure. As shown in FIG. 1, the struts 104 may be formed as a unitary structure from a single piece of material, such as a tubular member or a flat sheet of material. In some instances, the struts 104 may be laser cut from a tubular member or flat sheet of material. In other instances, the struts 104 may be formed of separate pieces (e.g., filaments) and attached to each other using known mechanisms such as melting, welding, etc., thereby forming a circumferential pattern around a longitudinal axis A to form the circumferential framework 102, or the separate pieces may be interwoven, braided, or otherwise arranged to form the framework 102. Voids between the struts or members 104 may form interstices 103.

In some instances, the framework 102 may include different patterns of struts 104 and/or interstices 103 along different portions of the length of the framework 102. For example, the size, shape, spacing, etc. of the interstices 103 may be varied along the length of the framework 102, such that a first (e.g., proximal) portion of the framework 102 may have a first configuration of interstices 103 (e.g., size, shape, spacing, etc.) and a second (e.g., distal) portion of the framework 102 may have a second configuration of interstices 103 (e.g., size, shape, spacing, etc.), different than the first configuration. In another example, a braided configuration of the stent 100 may include a first braid pattern along a proximal portion of the framework 102 and a second braid pattern along a distal portion of the framework 102, different from the first braid pattern, resulting in a variation of the interstice 103. Varying the pattern of struts 104 and/or interstices 103 may vary the radial force and/or flexibility of the framework 102 along the length of the stent 100.

In some instance, the interstices 103 may allow tissue ingrowth around the endoluminal stent 100 through the interstices 103. In other instances, the stent 100 may include a covering (e.g., a coating) across the interstices 103 to prevent tissue ingrowth. It is understood that the struts 104 in the framework 102 may have any desirable shape, permitting the framework 102 to expand and/or contract, as desired. In some embodiments, the number or arrangement of the struts 104 may be selected based on the rigidity or porosity of the framework 102. For example, the elongate framework 102 may include two, three, four, five, six, seven, eight, nine, ten, or more different patterns of struts 104 symmetrically or asymmetrically arranged around the circumference of the framework 102, as desired.

The framework 102 may be formed using any desired material, such as a metallic material or a polymeric material. In some instances, the interconnected struts 104 forming the framework 102 may be formed or cut from a thin metal or polymeric sheet with different patterns and rolled into a tubular configuration. In other embodiments, the struts 104 forming the framework 102 may be formed or cut from a metal or polymeric tubular member, with an elongate cut through the sidewall along one side to form a C-shaped framework 102. In some embodiments, the pattern of the struts 104 with the interstices 103 may facilitate radial compression or expansion (i.e., change in diameter) and/or elongation (i.e., change in length) of the framework 102. Thus, the framework 102 may be able to be compressed or expanded to fit the anatomy of the body lumen where it is implanted. The framework 102 of the stent 100 may be self-expandable or expandable by the application of an external applied force, such as a balloon positioned within the framework 102 exerting a radially outward force onto the framework 102.

In some embodiments, the framework 102 may be formed using metallic material, such as stainless steel, tungsten, etc. In some instances the metallic material may be a super elastic alloy or a shape memory alloy, such as nitinol. The framework 102 may be formed by cutting a nitinol tube or a flat sheet by a laser or another technique that is known in the art. The framework 102 may then be formed into a C-shape by known methods, thereby forming a C-shaped endoluminal stent. In some other embodiments, the framework 102 may be formed using any suitable method, such as, but not limited to, over molding, injection molding, dip molding, and so forth. In some other embodiments, the framework 102 may be formed using any biocompatible polymer, such as polyurethane, polyamide, silicone, or other desired polymeric material. In some instances, the framework 102 or other portion of the stent 100 may include one or more radiopaque elements attached to the stent 100, may be formed at least in part of a radiopaque material, and/or may include a radiopaque material incorporated into filaments or struts 104 to aid in visualization of the stent 100 within the anatomy of a patient.

Figure 2A:
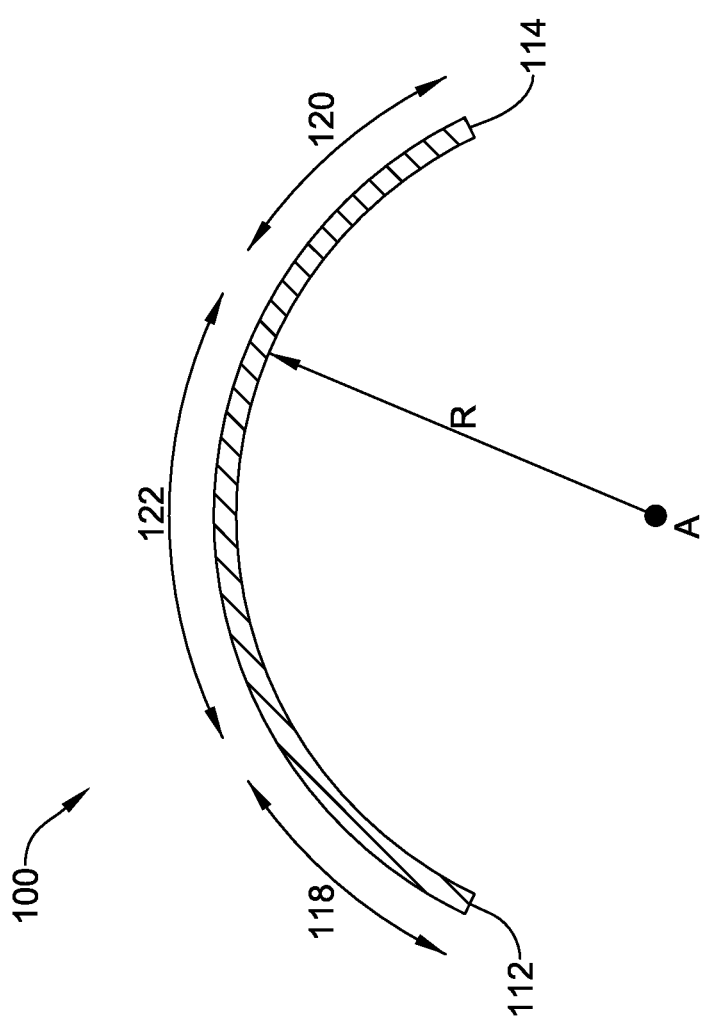
FIG. 2A is a cross-sectional view of the exemplary endoluminal stent of FIG. 1.

The framework 102 may have a C-shaped cross-section in a plane perpendicular to the longitudinal axis A to more closely conform to the cross-sectional shape of a trachea. An exemplary C-shaped cross-section of the endoluminal stent of FIG. 1 in a relaxed or unrestrained state is shown in FIG. 2A. As shown in FIG. 2A, the framework 102 may include a first edge region 118 that includes the first edge 112 and the surrounding area, and a second edge region 120 that includes the second edge 114 and the surrounding area. Further, the framework 102 may include an intermediate region 122 between the first edge region 118 and the second edge region 120. The framework 102 (at the intermediate region 122) may have a radius of curvature R in a relaxed or unrestrained state. The radius of curvature R may be equal to or greater than the radius of the trachea of a patient, for example.

Figure 2B:
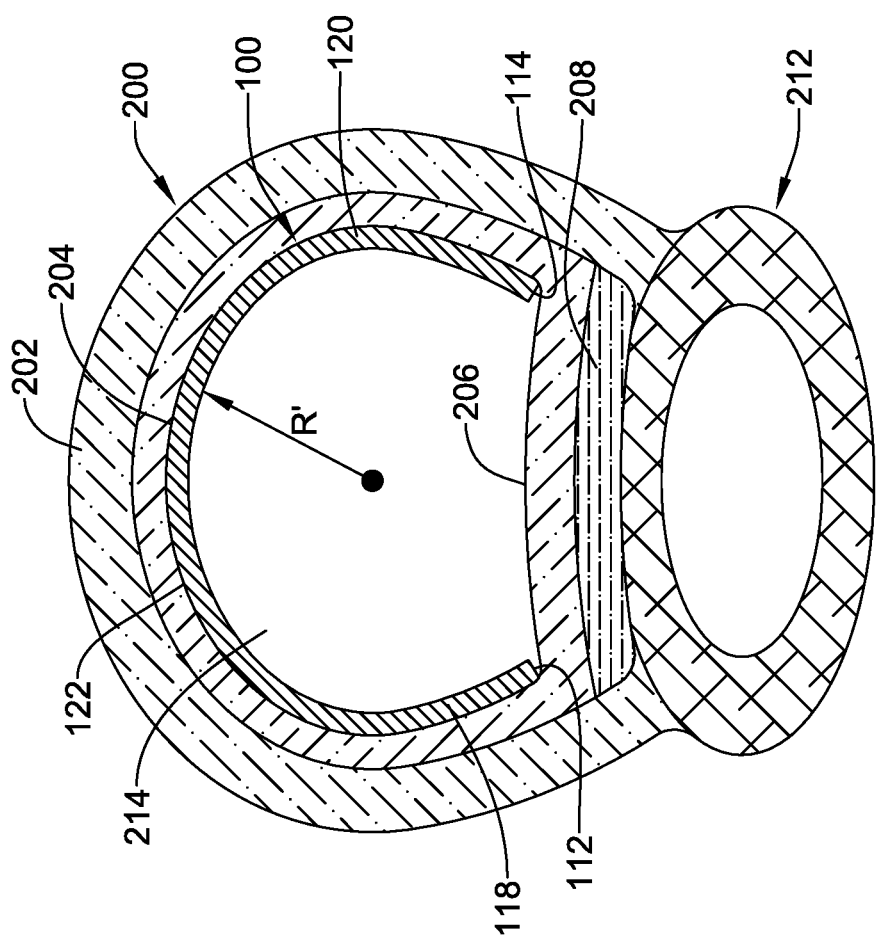
FIG. 2B is a top view of the exemplary endoluminal stent implanted in a trachea of a patient.

In some embodiments, the radius R of the framework 102 may be such that the framework 102 may be inserted in lumens of various sizes and geometry. For example, the opening 116 of the endoluminal stent 100 may be reduced by, for example, application of force to constrict the curvature of the framework 102 to a radius of curvature R' to fit within the trachea 200 of a patient, as shown in FIG. 2B. Thus, when implanted, the framework 102 may have a radius of curvature R' in a constricted or restrained state less than the radius of curvature R in an unrestrained state.

The trachea 200 is a passage that enables air to travel between the oral and nasal cavities into bronchi, in order to reach the lungs during breathing. The trachea 200 may include an anterior wall 204 and a posterior wall 206. The trachea 200 may have an elongated D-shaped cross-section with the flat posterior wall 206. Several C-shaped bars of the hyaline cartilage 202 prevent the trachea 200 from collapsing. The posterior wall 206 includes a trachealis muscle 208 that constricts into the lumen 214 of the trachea 200 to narrow the airway in order expel air from the trachea during a cough, and the anterior wall 204 includes cartilage rings. The trachea 200 is oriented anterior to the esophagus 212, with the trachealis muscle 208 positioned between the lumen 214 of the trachea and the esophagus 212.

As discussed above, in some instances the trachea 200 may be weakened by a disease, such as trachaeobronchomalacia (TBM), impinged by a tumor, injured by trauma, or otherwise impaired, and thus may require a support. For treatment, the endoluminal stent 100 may be inserted into a lumen 214 of the trachea 200 such that the intermediate region 122 of the endoluminal stent 100 may come in contact with the anterior wall 204 of the trachea 200 and the opening 116 between the first edge 112 and the second edge 114 may be positioned along the posterior wall 206 adjacent the trachealis muscle 208. Hence, the anterior wall 204 may be covered by the endoluminal stent 100 while the posterior wall 206 may be uncovered, thereby allowing the uncovered area to allow mucus clearing.

In some embodiments, the radius R of the endoluminal stent 100 may be equal to the radius r of the trachea 200 to provide the sufficient radial force and structure to the trachea 200. In some embodiments, the radius R of the endoluminal stent 100 may be larger than or smaller than the radius r of the trachea 200 to provide the sufficient radial force and support to the structure of the trachea 200.

Figure 3:
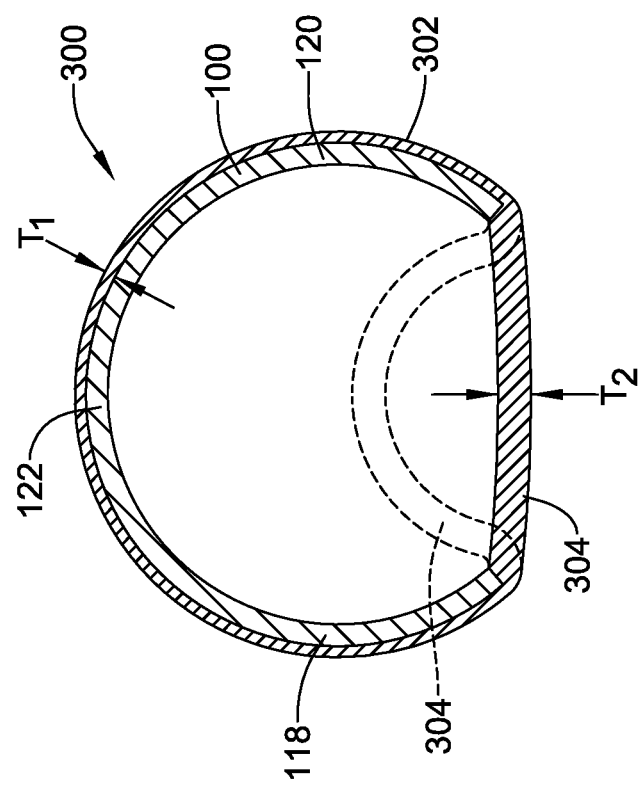
FIG. 3 is a cross-sectional view of an exemplary endoluminal stent with a covering.

FIG. 3 is a cross-sectional view of the exemplary endoluminal stent 100 with a covering layer 300. In some instances, the covering layer 300 may be configured to be disposed on the endoluminal stent 100 (e.g., on the framework 102) so that structures of the trachea may be maintained and tissue formation on the trachea 200 may be prevented. In some instances, the covering layer 300 may cover the framework 102 of the endoluminal stent 100 except for the open area of its C-shape (i.e., the opening 116). In other instances, a portion of the covering layer 300 may extend across the opening 116 of the framework 102 from the first edge 112 to the second edge 114. As shown in FIG. 3, the covering layer 300 may include a first portion 302 and a second portion 304. The first portion 302 may cover the struts 104 (the first edge region 118, the second edge region 120, and the intermediate region 122), as well as the interstices 103 of the framework 102. The second portion 304 may extend across the opening 116 of the framework 102, and thus may be positioned adjacent the posterior wall 206 of the trachea 200, thereby covering the endoluminal stent 100 fully. In some instances, the second portion 304 of the covering layer 300 extending across the opening 116 may be planar (e.g., may extend straight from the first edge 112 to the second edge 114). However, in some embodiments, the covering layer 300 may cover only the struts 104 and the interstices 103, if desired. As shown in FIG. 3, the first portion 302 may have thickness T1 and the second portion 304 may have thickness T2 different than the thickness T1. For example, the thickness T1 may be greater than or less than the thickness T2. In some embodiments, the second portion 304 may be thicker in the opening 116 of the C-shape, thereby resisting tumor ingrowth on the posterior wall 206 of the trachea 200.

In some embodiments, the covering layer 300 may be flexible providing comfort in swallowing and coughing to the patient. For example, as shown in phantom lines in FIG. 3, the covering layer 300 may deflect into the lumen of the stent 100 as the trachealis muscle contracts into the lumen of the trachea 200 during a cough.

In some embodiments, variation in thickness of the covering 300 may be achieved by any desired method. Examples of such methods may include but are not limited to spray coating, dip coating, or a combination of dip and spray coating, and so on.

In some embodiments, the covering 300 may be formed from a biocompatible material. Examples of such materials may include but are not limited to polymers such as silicone, polyvinylchloride, polyurethane, high-density polyethylene (HDPE), low-density polyethylene (LDPE), as well as other biocompatible polymer materials.

Figure 4A:
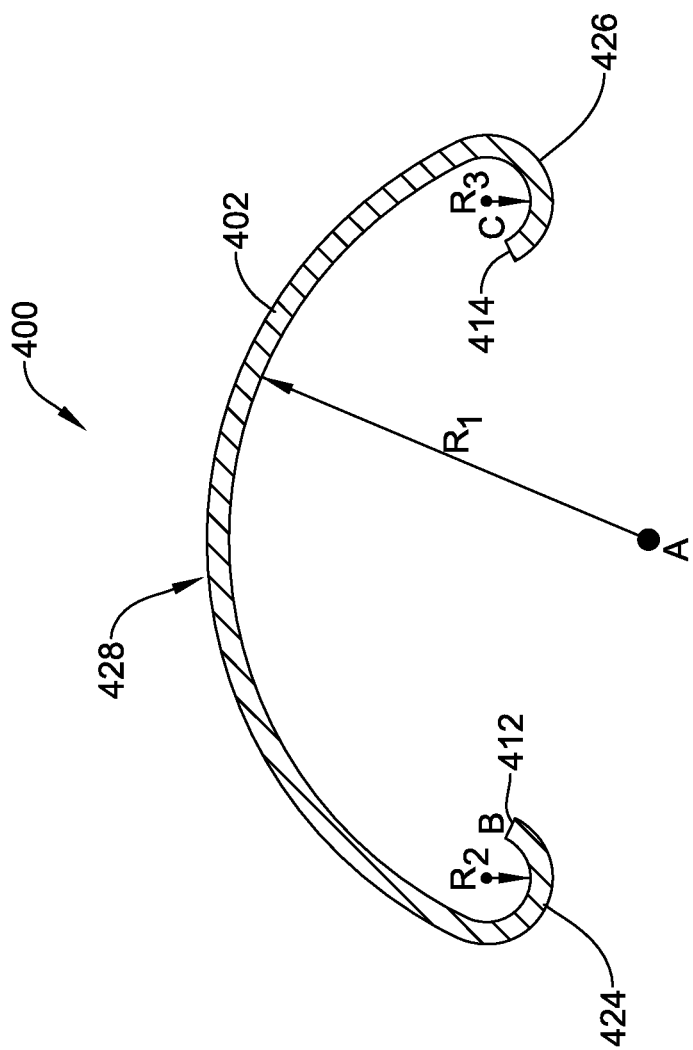
FIG. 4A illustrates another embodiment of an exemplary endoluminal stent, in accordance with some embodiments of the present disclosure.

FIG. 4A is a cross-sectional view of another embodiment of an exemplary endoluminal stent 400. The structure of the endoluminal stent 400 may be similar to the endoluminal stent 100 except described below herein. The endoluminal stent 400 may include an elongate framework 402 including a first edge 412 extending from the first open end to the second open end, a second edge 414 extending from the first open end to the second open end, and an opening 416 (see FIG. 4B) between the first edge 412 and the second edge 414 extending from the first open end to the second open end such that the stent 400 has a C-shaped cross-section.

The C-shaped cross-section of the framework 402 of the endoluminal stent 400 may include a first curled end region 424, a second curled end region 426, and a central arcuate portion 428 extending between the first and second curled end regions 424, 426. The central arcuate portion 428 may have a primary radius of curvature $R_1$ about a longitudinal axis A extending from the first open end of the endoluminal stent 400 to the second open end of the endoluminal stent 400. The first curled end region 424 may have a first secondary radius of curvature $R_2$ about a longitudinal axis B extending through the lumen of the framework 402. The second curled end region 426 may have a second secondary radius of curvature $R_3$ about a longitudinal axis C extending through the lumen of the framework 402. The longitudinal axes B and C may be parallel to the longitudinal axis A, if desired. In some embodiments, the radii of curvatures $R_2$, $R_3$ of the first and second curled end regions 424, 426 may be less than the radius of curvature $R_1$ of the central arcuate portion 428. Hence, the first and second curled end regions 424, 426 may be curled or turned inward toward the center of the endoluminal stent 400. In some instances, the radii of curvature $R_2$, $R_3$ at the edges 412, 414 may approximate the radius between the cartilage rings and trachealis muscle of the trachea during a cough (see FIG. 4C) to resist collapse and further prevent granulation tissue formation.

Figure 4B:
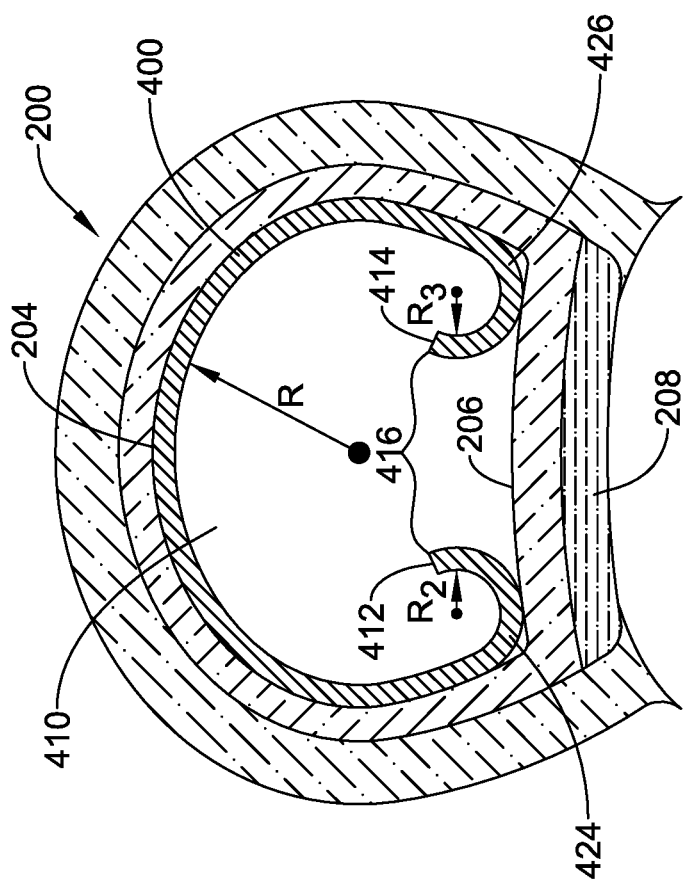
FIG. 4B is a top view of the exemplary endoluminal stent of FIG. 4A implanted in a trachea of a patient.

As shown in FIG. 4B, the endoluminal stent 400 may be placed in the trachea 200 in a similar way to that of the endoluminal stent 100. For example, the endoluminal stent 400 may be implanted in the trachea 200 with the opening 416 between the edges 412, 414 positioned along the posterior wall 206 of the trachea 200 adjacent the trachealis muscle 208. In this orientation, the endoluminal stent 400 may cover the anterior wall 204 of the trachea 200 while the posterior wall 206 of the trachea 200 may remain uncovered.

Figure 4C:
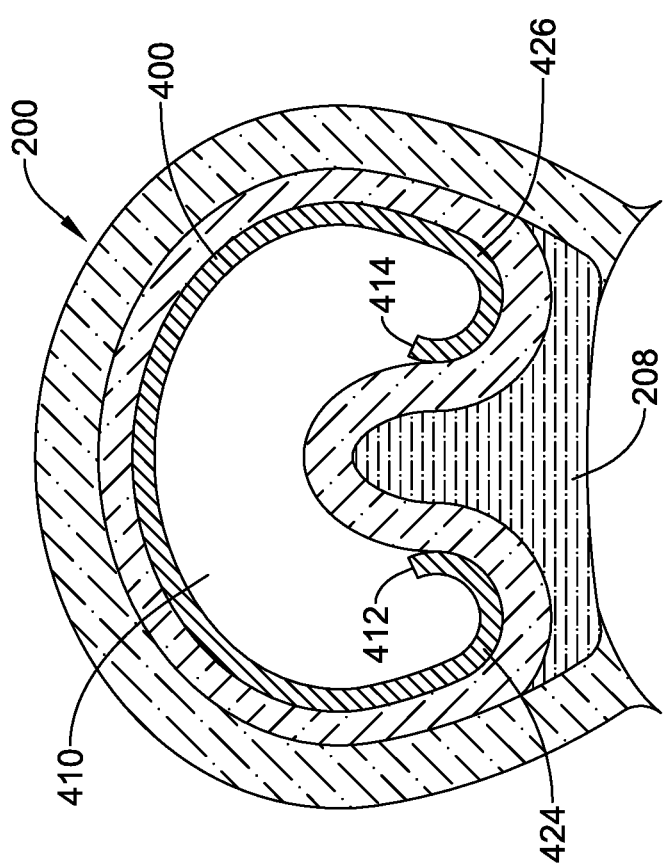
FIG. 4C is a top view of the exemplary endoluminal stent of FIG. 4A implanted in a trachea of a patient during coughing.

During coughing, for example, the trachealis muscle 208 may contract into the lumen of the trachea 200 such that the uncovered posterior wall 206 of the trachea 200 may deflect towards the lumen 410 of the endoluminal stent 400. Thus, a portion of the posterior wall 206 may deflect towards the lumen 410 and follow the curvature of the first and second curled end regions 424, 426, as shown in FIG. 4C. Hence, the radii of curvature $R_2$, $R_3$ at the first and second curled end regions 424, 426 may be designed in a way that the radii at the edges 412, 414 may match or approximate the radius of the trachea 200 between the cartilage rings and the trachealis muscle 208 during a cough to resist collapse and further prevent granulation tissue formation.

If it is desired to remove or reposition the endoluminal stent 400, the first and second curled end regions 424, 426 may be drawn toward one another with a medical device (e.g., forceps) to constrain the stent 400. The first and second curled end regions 424, 426 may provide easy features to grab for removal of the endoluminal stent 400 via forceps or grasping tool (not shown). The first and second curled end regions 424, 426 may be grabbed with the forceps, followed by twisting to reduce outer diameter and then may be pulled out, for example.

Figure 5A:
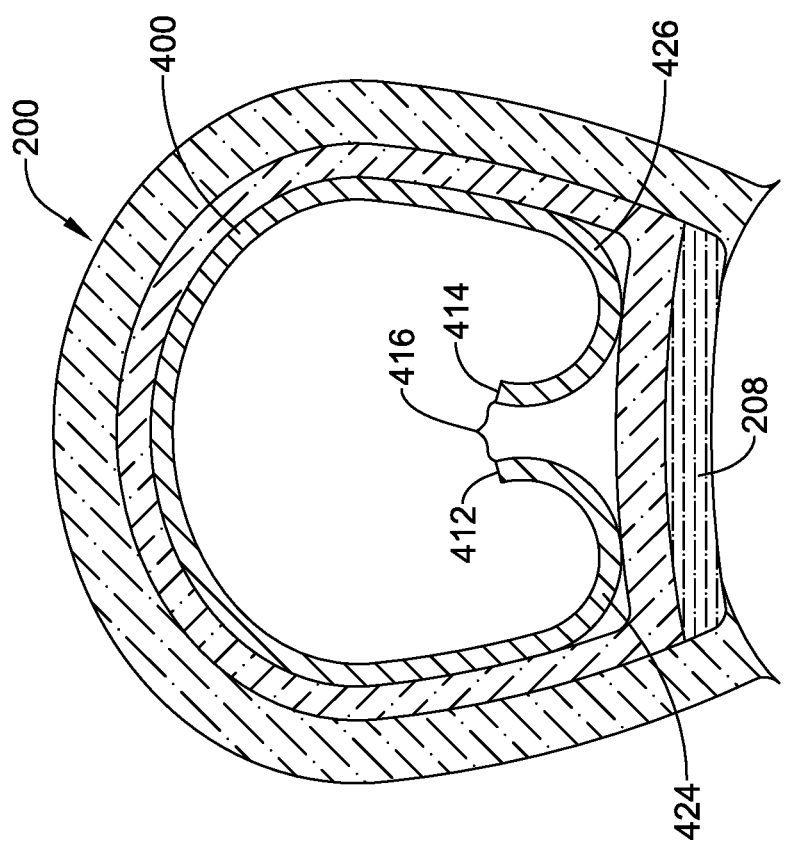
FIGS. 5A and 5B are cross-sectional views of the exemplary endoluminal stent of FIG. 4A implanted in a trachea where first and second edge regions are drawn toward one another.
Figure 5B:
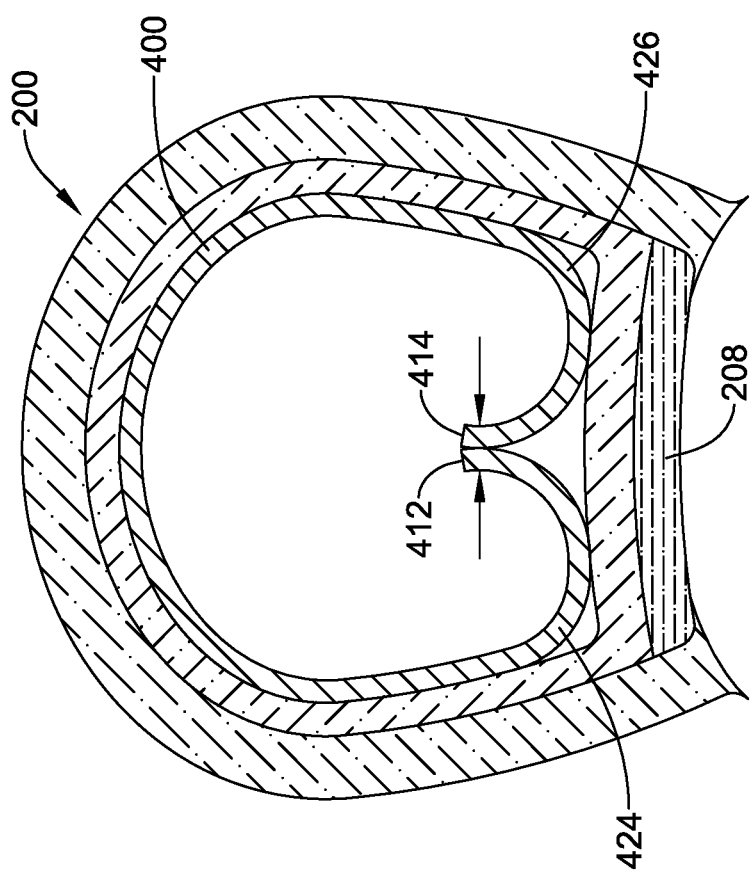

In some embodiments, the first and second curled end regions 424, 426 may provide additional rigidity to the endoluminal stent 400 and resist tumors or other obstructions in the trachea. For example, as shown in FIG. 5A, the first and second curled end regions 424, 426 may have radii of curvature that brings the end regions 424, 426 close to one another while maintaining a gap or opening 416 therebetween. As shown in 5B, if the trachea 200 is compressed by growth of a tumor, the first and second curled end regions 424, 426 may come in contact with each other and thereafter prevent further collapse of the stent 400 and thus provide additional resistance against the tumor. Such contact between the first and second curled end regions 424, 426 may provide a strong radial resistance force but also allow for a fluid drainage channel between the endoluminal stent 400 and the lumen wall of the trachea 200.

Figure 6:
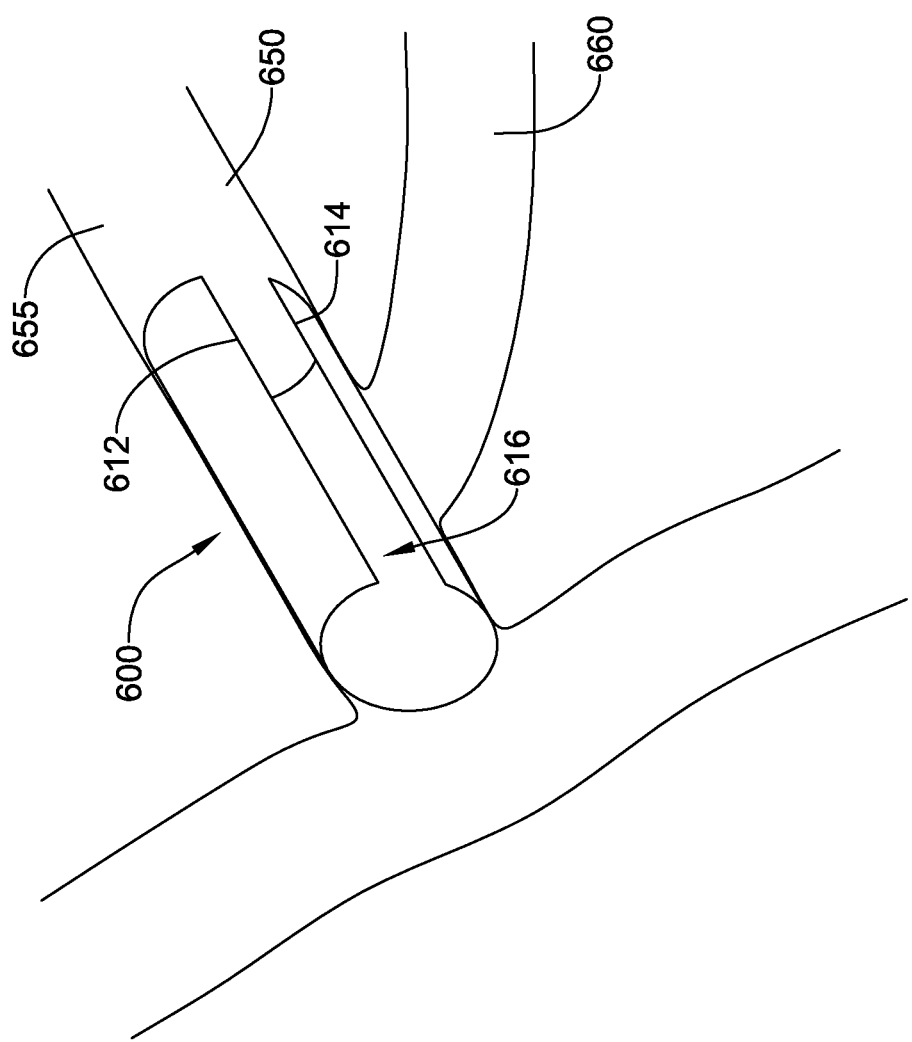
FIG. 6 illustrates a perspective view of implantation of an exemplary endoluminal stent implanted in bronchi.

FIG. 6 illustrates a perspective view of an exemplary endoluminal stent 600 near a luminal branch, such as a branch region of bronchi 650. However, in some embodiments, the endoluminal stent 600 may be employed in a bifurcation of a vessel, bile duct, hepatic duct, or other bifurcations. The endoluminal stent 600 may be similar to that of the endoluminal stent 100 or the endoluminal stent 400. Insertion of the endoluminal stent 600 in a lumen 655 of a bronchi (or other lumen) may allow stenting without blockage of the side-branching lumen 660. For example, the opening 616 between the first edge 612 and the second edge 614 may be positioned toward the side-branching lumen 660, such that the opening 616 opens into the side-branching lumen 660. In some embodiments, the insertion may also allow fluid (e.g., air) to pass through the side branching lumen 660 from the main lumen 655.

Figure 7:
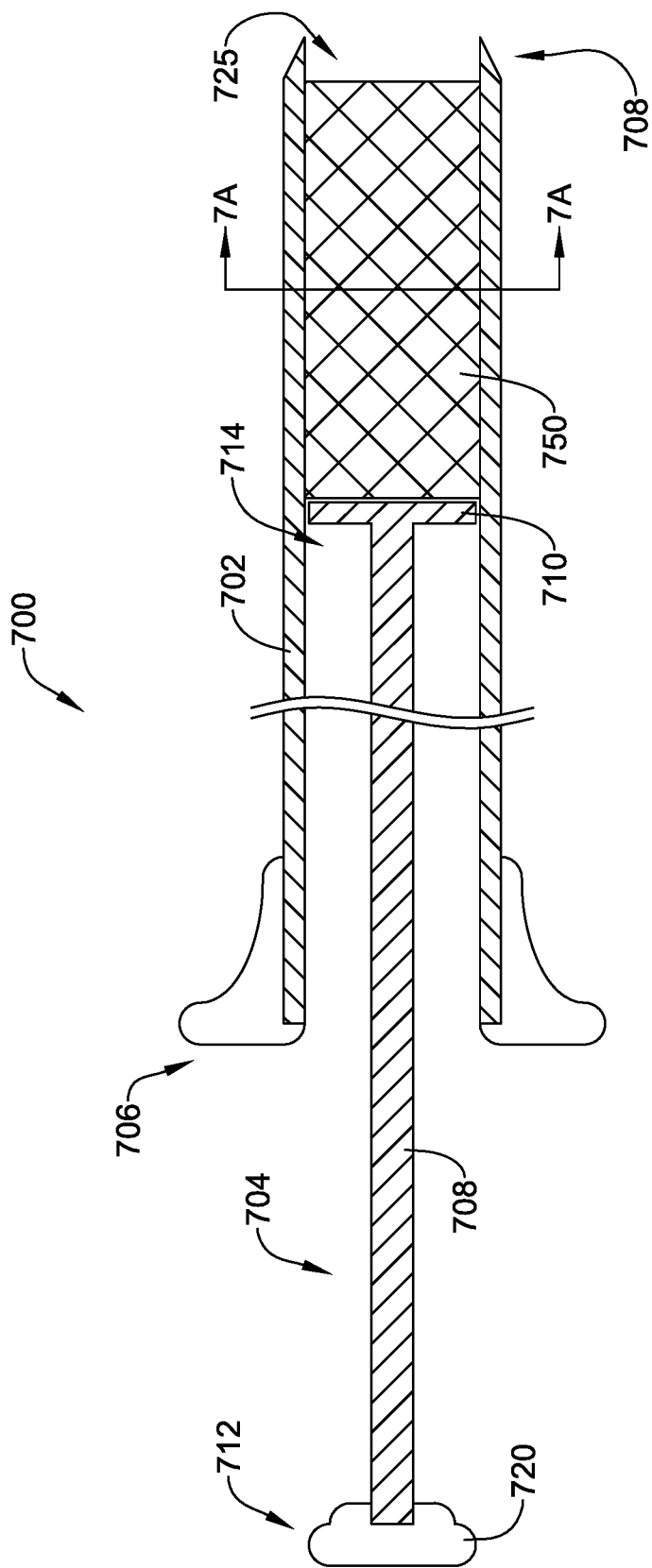
FIG. 7 illustrates an exemplary delivery system for placing an exemplary stent in a body lumen, such as the lumen of a trachea.

FIG. 7 illustrates a delivery system 700 to deliver an exemplary endoluminal stent in a lumen of a trachea. The delivery system 700 may include an outer member or sheath 702 and an inner member or pusher 704. The sheath 702 may be an elongated member having a proximal end 706, a distal end 708, and a lumen 725 extending from the proximal end 706 to the distal end 708. The sheath 702 may be configured to receive an endoluminal stent 750 in a collapsed state and deliver the endoluminal stent 750 at a target location. The endoluminal stent 750 may be an endoluminal stent as described above.

The endoluminal stent 750 may be loaded into the lumen 725 by any desired means. For example, the endoluminal stent 750 may be introduced in the lumen 725 from the distal end 708 of the sheath 702. In some instances, the structure of the endoluminal stent 750 may be similar to the endoluminal stent 100 or 400, if desired.

Further, the delivery system 700 may include an inner member or pusher 704 extending through the lumen 725 of the sheath 702. The pusher 704 may be actuated relative to the sheath 702 to create a push-pull mechanism. The pusher 704 may include an elongate shaft 708 having a handle 720 at a proximal end 712 thereof and an engagement member 710 at a distal end 714 thereof configured to engage the endoluminal stent 750. The engagement member 710 may be configured to deploy the endoluminal stent 750 upon actuation of the shaft 708 relative to the sheath 702. The handle 720 may be disposed at the proximal end 712 of the shaft 708 and may be configured to be held by an operator to actuate the pusher 704. Once the physician actuates the pusher 704, the engagement member 710 may push the endoluminal stent 750 distally out of the lumen 725 thereby deploying the endoluminal stent 750.

In some instances the delivery system 700 may include a delivery mechanism including members configured to engage the curved edges of the stent 750 and pull the curved edges of the stent 750 together to reduce the profile of the stent 750.

Figure 7A:
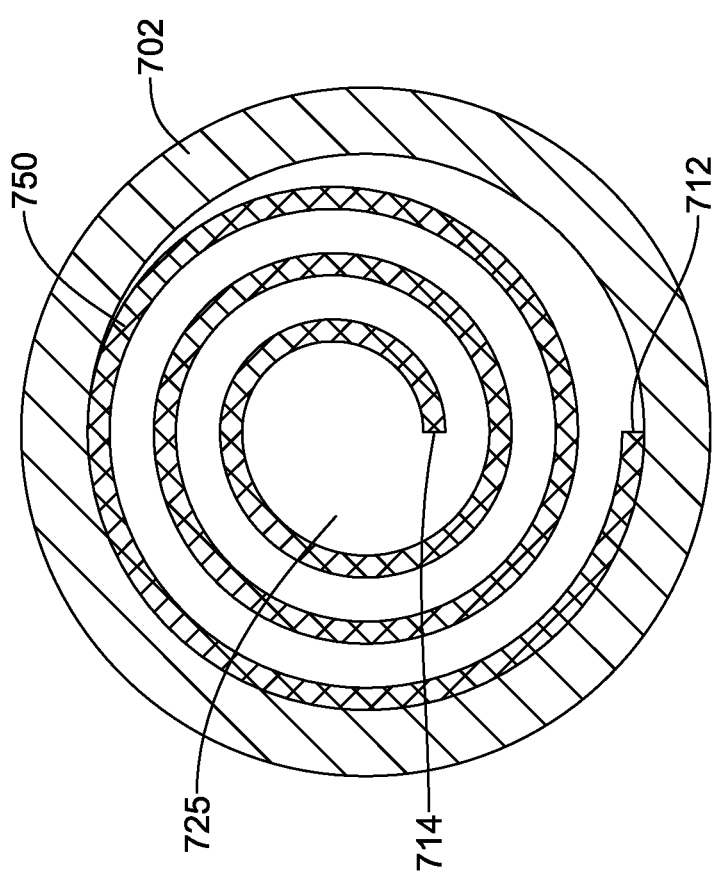
FIG. 7A is a cross-sectional view taken along line 7A-7A of FIG. 7 illustrating an exemplary endoluminal stent in a delivery configuration.

FIG. 7A illustrates a cross-sectional view of the sheath 702 including the endoluminal stent 750 taken along line 7A-7A of FIG. 7. The endoluminal stent 750 may be placed in the sheath 702 in a collapsed state. For example, in some embodiments, the endoluminal stent 750 may be curled and compressed down to a small diameter for delivery into a trachea, vessel, or other lumen in which the endoluminal stent 750 may be placed. Since the endoluminal stent 750 may have a first edge 712 extending longitudinally from a first end to a second end of the endoluminal stent 750, and a second edge 714 extending longitudinally from the first end to the second end of the endoluminal stent 750, the stent 750 may be rolled up into a tight spiral to reduce the delivery diameter of the stent 750, for example. Thus, the first edge 712 may overlap with the second edge 714 in a constricted, delivery configuration within the lumen 725 of the delivery system 700.

A method of placing an exemplary endoluminal stent in a lumen of the trachea may include a number of consecutive, non-consecutive, simultaneous, non-simultaneous, or alternative steps. The method may include inserting the endoluminal stent into the lumen of the trachea. The method may further include orienting the endoluminal stent in the lumen of the trachea. The endoluminal stent may be oriented such that the opening of the endoluminal stent may be positioned along a posterior wall of the trachea adjacent a trachealis muscle.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one exemplary embodiment in other embodiments. The disclosure's scope is, of course, defined in the language in which the appended claims are expressed.

ADDITIONAL EXAMPLES

A first example includes an endoluminal stent comprising an elongate framework. The elongate framework has a first open end, a second open end opposite the first open end, and a lumen extending from the first open end to the second open end. The elongate framework also includes a first edge extending from the first open end to the second open end, a second edge extending from the first open end to the second open end, and an opening between the first edge and the second edge. The opening extends continuously from the first open end to the second open end.

Additionally or alternatively, in a second example, the elongate framework is formed of a plurality of interconnected struts defining interstices therebetween.

Additionally or alternatively, in a third example, the elongate framework includes a first edge region proximate the first edge extending from the first open end to the second open end, a second edge region proximate the second edge extending from the first open end to the second open end, and an intermediate region between the first and second edge regions extending from the first open end to the second open end. The intermediate region has a primary radius of curvature about a primary longitudinal axis extending through the lumen, the first edge region has a first secondary radius of curvature about a first secondary longitudinal axis extending through the lumen, and the second edge region has a second secondary radius of curvature about a second secondary longitudinal axis extending through the lumen. The first secondary radius of curvature and the second secondary radius of curvature are less than the primary radius of curvature.

Additionally or alternatively, in a fourth example, the endoluminal stent is configured to be positioned in a trachea with the opening oriented toward a posterior wall of the trachea.

Additionally or alternatively, in a fifth example, the first and second edges are configured to be drawn toward one another with a medical device to remove the endoluminal stent from a body lumen.

Additionally or alternatively, in a sixth example, the first and second edge regions are configured to abut one another to resist radial contraction of the endoluminal stent in a body lumen.

Additionally or alternatively, in a seventh example, the endoluminal stent includes a covering layer covering at least a portion of the elongate framework.

Additionally or alternatively, in an eighth example, the covering layer includes a first portion covering the interconnected struts and interstices of the elongate framework, and the covering layer includes a second portion extending across the opening between the first and second edges of the elongate framework. The first portion has a first thickness and the second portion has a second thickness different than the first thickness. In some instances, the second thickness is greater than the first thickness, whereas in other instances the second thickness is less than the first thickness.

Additionally or alternatively, in a ninth example, the covering layer extends across the opening between the first and second edges of the elongate framework.

Additionally or alternatively, in a tenth example, the covering layer extends across the opening is generally planar.

Additionally or alternatively, in an eleventh example, the endoluminal stent is configured to be implanted in a trachea, and the covering layer extending across the opening is configured to deflect into the lumen of the elongate framework during a cough.

Additionally or alternatively, in a twelfth example, the elongate framework has a C-shaped cross section in a plane perpendicular to a longitudinal axis of the elongate framework.

Additionally or alternatively, in a thirteenth example, the C-shaped cross section of the elongate framework includes a first curled end region, a second curled end region and a central arcuate portion between the first and second curled end regions.

Additionally or alternatively, in a fourteenth example, the first and second curled end regions have a radius of curvature less than a radius of curvature of the central arcuate portion.

What is claimed is:

1. An endoluminal stent, comprising:
an elongate framework including a plurality of interconnected struts extending along an entire length of the stent, wherein the elongate framework further includes a first edge extending along the entire length of the stent, a second edge extending along the entire length of the stent, and an arcuate portion extending between the first edge and the second edge;
wherein the arcuate portion includes a C-shaped concave inner surface extending from the first edge to the second edge;
wherein the first edge includes a first curled portion, the second edge includes a second curled portion, and wherein each of the first curled portion and the second curled portion are positioned adjacent to the concave inner surface.

2. The stent of claim 1, wherein the arcuate portion includes a central region, and wherein the first curled portion and the second curled portion are turned inward toward the central region.

3. The stent of claim 1, wherein the C-shaped concave inner surface extends continuously along the entire length of the stent.

4. The stent of claim 1, wherein the elongate framework comprises interconnected struts and interstices formed therebetween.

5. The stent of claim 1, wherein the stent is configured to be implanted in a trachea, wherein the C-shaped concave inner surface of the arcuate portion is configured to face a posterior wall of the trachea.

6. The stent of claim 1, wherein the C-shaped concave inner surface includes a first radius of curvature, wherein the first curled portion includes a second radius of curvature, wherein the second curled portion includes a third radius of curvature and wherein the second radius of curvature and third radius of curvature are different than the first radius of curvature.

7. The stent of claim 6, wherein the second radius of curvature and third radius of curvature are less than the first radius of curvature.

8. The stent of claim 1, wherein the first and second edge regions are configured to be drawn toward one another with a medical device to remove the stent from a body lumen.

9. An endoluminal stent, comprising:
an elongate framework including a plurality of interconnected struts extending along a length of the stent from a first end of the elongate framework to a second end of the elongate framework, wherein the elongate framework further includes a first edge extending along the length of the stent from the first end of the elongate framework to the second end of the elongate framework, a second edge extending along the length of the stent from the first end of the elongate framework to the second end of the elongate framework, and an arcuate portion extending between the first edge and the second edge;
the arcuate portion defines a concave inner surface;
wherein the first edge and the second edge of the arcuate portion do not overlap;
wherein the first edge includes a first curled portion, the second edge includes a second curled portion, and wherein each of the first curled portion and the second curled portion are positioned adjacent to the concave inner surface.

10. The stent of claim 9, wherein the arcuate portion includes a central region, and wherein the first curled portion and the second curled portion are turned inward toward the central region.

11. The stent of claim 9, wherein the concave inner surface extends continuously along the length of the stent from the first end of the elongate framework to the second end of the elongate framework.

12. The stent of claim 9, wherein the elongate framework comprises interconnected struts and interstices formed therebetween.

13. The stent of claim 9, wherein the stent is configured to be implanted in a trachea, wherein the concave inner surface of the arcuate portion is configured to face a posterior wall of the trachea.

14. The stent of claim 9, wherein the concave inner surface includes a first radius of curvature, wherein the first curled portion includes a second radius of curvature, wherein the second curled portion includes a third radius of curvature and wherein the second radius of curvature and third radius of curvature are different than the first radius of curvature.

15. The stent of claim 14, wherein the second radius of curvature and third radius of curvature are less than the first radius of curvature.

16. The stent of claim 9, wherein the first edge and the second edge are configured to be drawn toward one another with a medical device to remove the stent from a body lumen.

17. An endoluminal stent, comprising:
an elongate framework including a plurality of interconnected struts extending along an entire length of the stent,
wherein the elongate framework further includes an arcuate portion having a concave inner surface;
a first inwardly curled edge extending along the entire length of the stent adjacent the arcuate portion; and
a second inwardly curled edge extending along the entire length of the stent adjacent the arcuate portion,
wherein the first inwardly curled edge and the second inwardly curled edge do not overlap and are opposed across a gap when the stent is in an unconstrained configuration.

18. The endoluminal stent of claim 17, wherein the arcuate portion having a concave inner surface defines a first radius of curvature,
wherein the first inwardly curled edge defines a second radius of curvature,
wherein the second inwardly curled edge defines a third radius of curvature and wherein the second radius of curvature and the third radius of curvature are the same as each other, and both the second radius of curvature and the third radius of curvature are less than the first radius of curvature.

* * * * *